United States Patent [19]

Denis et al.

[11] Patent Number: 5,250,203
[45] Date of Patent: * Oct. 5, 1993

[54] LUBRICATING OIL COMPOSITIONS CONTAINING A POLYOXYALKYLENE CARBOXYLIC ACID SALT ADDITIVE

[75] Inventors: Richard A. Denis, Eastlake; Frederick W. Koch, Willoughby Hills, both of Ohio

[73] Assignee: The Lubrizol Corporation, Wickliffe, Ohio

[*] Notice: The portion of the term of this patent subsequent to Nov. 15, 2005 has been disclaimed.

[21] Appl. No.: 834,756

[22] Filed: Feb. 12, 1992

Related U.S. Application Data

[63] Continuation of Ser. No. 746,526, Aug. 16, 1991, abandoned, which is a continuation of Ser. No. 554,614, Jul. 18, 1990, abandoned, which is a continuation of Ser. No. 263,578, Oct. 27, 1988, Pat. No. 4,954,273, which is a continuation of Ser. No. 20,287, Feb. 27, 1987, Pat. No. 4,784,781.

[51] Int. Cl.$^5$ ............... C10M 129/32; C10M 129/40; C10M 129/66; C10M 129/93
[52] U.S. Cl. ................................ 252/18; 252/34; 252/35; 252/38; 252/39; 252/40; 252/41
[58] Field of Search ................. 252/18, 34, 35, 38, 252/39, 40, 41

[56] References Cited

U.S. PATENT DOCUMENTS

| | | | |
|---|---|---|---|
| 2,801,972 | 8/1957 | Bartlett et al. | 252/41 |
| 3,625,893 | 12/1971 | Brook et al. | 252/32.7 |
| 3,791,971 | 2/1974 | Lowe | 252/33.4 |
| 3,828,086 | 8/1974 | Kenny et al. | 252/39 |
| 3,856,688 | 12/1974 | Kenny et al. | 252/39 |
| 4,088,590 | 5/1978 | Knoblauch et al. | 252/73 |
| 4,265,774 | 5/1981 | Langdon | 252/49.3 |
| 4,579,672 | 4/1986 | Brecker | 252/49.8 |
| 4,784,781 | 11/1988 | Denis | 252/39 |
| 4,954,273 | 9/1990 | Denis et al. | 252/39 |

FOREIGN PATENT DOCUMENTS

| | | |
|---|---|---|
| 0018681 | 11/1980 | European Pat. Off. |
| 0039111 | 11/1981 | European Pat. Off. |
| 0125144 | 11/1984 | European Pat. Off. |
| 2088863 | 6/1982 | United Kingdom |
| 2152050 | 7/1985 | United Kingdom |

OTHER PUBLICATIONS

Swalkeer and Smith, "Lubricant Additives", 1967, pp. 1-11.

*Primary Examiner*—Jerry D. Johnson
*Attorney, Agent, or Firm*—David M. Shold; Forest L. Collins

[57] ABSTRACT

Oil based compositions are disclosed which are comprised of oil having a multi-functional additive component therein. The additive component is present in sufficient amounts so as to provide improved performance characteristics to the composition such as water tolerance and antiwear characteristics. The additive is a compound represented by the general structural formula (I):

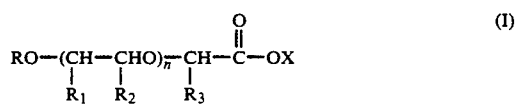

wherein R is a hydrocarbyl, preferably iso-stearyl, $R_1$, $R_2$, and $R_3$ are independently hydrogen or alkyl, preferably hydrogen, n is 1 to 20, preferably 5, and X is a cation, preferably Ca. Overbased and mixed salts of the additive compound are also disclosed. The additive is an effective EP agent, water tolerance fix in a variety of functional fluids and lubricating compositions.

20 Claims, No Drawings

LUBRICATING OIL COMPOSITIONS CONTAINING A POLYOXYALKYLENE CARBOXYLIC ACID SALT ADDITIVE

This is a continuation of copending application(s) Ser. No. 07/746,526 filed on Aug. 16, 1991; now abandoned which is a continuation of 07/554,614 filed on Jul. 18, 1990; now abandoned which is a continuation of 07/263,578 field Oct. 27, 1988 which issued as U.S. Pat. No. 4,954,273 on Sep. 4, 1990; which is a continuation of 07/020,287 filed Feb. 27, 1987 which issued as U.S. Pat. No. 4,784,781 on Nov. 15, 1988.

FIELD OF THE INVENTION

The invention relates to the field of lubricants containing a multifunctional additive which improves the water tolerance characteristic of the lubricant without impacting adversely on extreme pressure/anti-wear properties. More specifically the invention relates to functional fluids having therein salts of iso-stearylpentaethylene glycol-acetic acid.

BACKGROUND OF THE INVENTION

Most lubricants and functional fluids are easily contaminated with water. Accordingly water compatibility is a highly significant property of functional fluids and lubricants. The significance of this property is most important under severe conditions such as when functional fluids and lubricants come into contact with water under extreme pressure and temperature conditions.

In the absence of acceptable water tolerance properties, such functional fluids and lubricants will have its lubricating and/or power transmission properties substantially reduced. Fluid flow is not smooth when water separates out and the separated water can be vaporized to steam at high temperature. Accordingly, many manufacturers of equipment requiring the use of functional fluids and lubricants require that such fluids and lubricants process specific water tolerance properties. For example, manufacturers of agricultural tractor machinery have specific requirements with respect to the tractor fluids used in connection with the machinery; and, such requirements include specific water tolerance properties which the manufacturer believes to be necessary for the equipment to operate successfully under severe conditions.

In addition, a fluid with poor water tolerance properties becomes turbid and the clarity of functional fluids often impacts greatly on the fluid's marketability. A fluid that is turbid or becomes turbid after a short period of use is often unacceptable to consumers regardless of the performance characteristics of the fluid. Improved clarity not only increases marketability but allows the user to more readily and accurately determine when the fluid should be replaced.

U.S. Pat. No. 4,579,672 discloses functional fluids and lubricants having improved water tolerance properties. The compositions are comprised of major amounts of a synthetic or mineral oils of lubricating viscosity with minor amounts of oil soluble alkoxypolyethyleneoxy acid phosphite ester compounds dispersed therein as the water tolerance improving compounds.

U.S. Pat. No. 3,791,971 discloses polyoxyalkylene glycols and their reaction products with organic diisocyanate and dicarboxylic acid. These reaction products are combined with alkaline earth metal carbonates and dispersed in a hydrocarbon medium to provide lubricating compositions which are indicated as having superior acid neutralization capability and rust inhibiting properties when used within internal combustion engines. A number of compounds are disclosed throughout the 3,791,971 patent such as those encompassed by the general structural formulation shown at column 2, lines 44-55.

U.S. Pat. No. 4,265,774 discloses high molecular weight polygylcerol derivatives which are indicated as being useful as thickening agents for water-based lubricants. A large number of compounds encompassed by the general structural formula as shown at column 1, lines 35-45 are disclosed.

U.S. Pat. No. 3,625,893 discloses lubricating oil compositions which include minor amounts of basic group II metals salts of carboxylic acids and napthenic acids. The oil compositions including the additives are indicated as having improved oxidation stability and antirust properties.

U.S. Pat. No. 4,088,590 discloses brake fluids and operating fluids for central hydraulic installations in motor vehicles which are indicated as having excellent temperature/viscosity behavior as well as good lubricating properties. The improved properties are indicated as being obtained by including additives in the form of polyethylene glycol alkyl ether-based fluids of alkyl polyethylene glycol-t-butyl ethers. Amounts of the additive and a structural formula encompassing the additive is shown within the 4,088,590 patent at column 1, lines 7-19.

The present inventors have discovered that improved functional fluids and lubricating compositions can be obtained by combining major amounts of an oil of lubricating viscosity with a minor amount of an additive component. In this respect, the present invention relates to the same general concept which is being carried out in the patents discussed above. However, the compounds which the present inventors utilize as the additive component is structurally different from and chemically distinct from the compounds referred to in the above-discussed patents. Although some of the compounds per se utilized by the present inventors to improve performance properties of compositions may not be completely novel compounds per se, such compounds as included within the oil compositions are novel compositions.

Sandoz Product Bulletin 7-200/85 refers to a number of surfactant compounds sold under the trademark Sandopan. These compounds generally conform to the formula:

where R is a fatty group containing 13 to 18 carbons, n is 2 to 4, m is 1 to 100, $R_1$ is $CH_2$ to $C_3H_6$ and X is H or Na. These compounds are indicated as being useful in products such as cleaning fluids, cosmetics and toiletries.

SUMMARY OF THE INVENTION

The present invention is based on the discovery by the present inventors that certain performance properties of oil based lubricating compositions can be improved by including within the composition small amounts of an additive compound represented by the general formula (I):

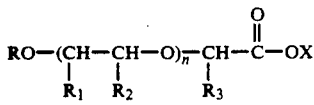

wherein R is a hydrocarbyl containing 1 to 44 carbons, $R_1$, $R_2$, and $R_3$ are independently hydrogen or an alkyl moiety containing 1 to 21 carbons, n is in the range of from 1 to 20, and X is a cation.

A primary object of the present invention is to provide a lubricating composition comprised of an oil of lubricating viscosity having therein an additive which increases the performance characteristic of the composition.

Another object is to provide such a composition wherein the additive is in the form of a compound of formula (I):

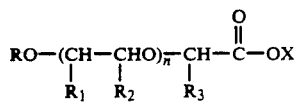

wherein R is a hydrocarbyl containing 1 to 44 carbons, $R_1$, $R_2$, and $R_3$ are independently hydrogen or an alkyl moiety containing 1 to 21 carbons, n is in the range of from 1 to 20, and X is a cation.

An advantage of the present invention is the additive compound provides an improvement in more than one performance characteristic of the composition.

Another advantage of the present invention is that the additive compound provides improvement with respect to water tolerance properties while not adversely affecting the anti-wear or frictional properties of the composition.

A feature of the present invention is that the additive compound reduces turbidity of fluids having contaminant water therein.

Another feature of the present invention is that the additive is effective in reducing wear and corrosion under extreme temperature and pressure conditions.

Another feature of this invention is that it provides improved water compatibility to functional fluids and lubricating compositions which are subjected to severe operational conditions.

Another advantage of this invention is that the additive compound can be included within an oil of lubricating viscosity in relatively small amounts at a relatively low cost.

Another feature of the present invention is that the functional fluids and lubricating compositions of the invention with the additive compound therein meet various agricultural machinery manufactures' specifications with respect to water tolerance properties.

Yet another feature of the present invention is that it provides a composition having a relatively high degree of clarity which can be maintained with contaminant water under severe operational conditions.

Another feature of the invention is that it aids in preventing water separation and thus aids in preventing water vaporization under high temperature conditions.

Another advantage of the invention is that it provides an additive which can be included in systems contaminated with water in order to provide improved water tolerance properties and reduced turbidity.

Still another advantage of the present invention is that the additive compounds disclosed can be overbased.

Still another feature of the invention is that the overbased additive compounds of the invention provide a means of reducing acidity in the system in which they are used.

These and other objects advantages and features of the present invention will become apparent to those persons skilled in the art upon reading the details of the structure synthesis and usage as more fully set forth below. Reference being made to the accompanying general structural formulae forming a part hereof wherein like symbols refer to like molecular moieties throughout.

DETAILED DESCRIPTION OF THE PREFERRED EMBODIMENTS OF THE INVENTION

Before the present oil based compositions containing the additive of the invention processes for making such are described, it is to be understood that this invention is not limited to the particular compositions, additives or processes described as such may vary. It is also to be understood that the terminology used herein is for the purpose of describing particular embodiments only, and is not intended to be limiting since the scope of the present invention will be limited only by the appended claims.

The present inventors have determined that it is possible to greatly improve the water tolerance characteristics of various compositions such as lubricating oils and functional fluids by including a particular additive compound therein. More specifically, the present inventors discovered that the water tolerance, antiwear and other characteristics of a composition can be improved by including therein an additive such as iso-stearylpentaethyleneglycol-acetic acid and salts thereof. Related compounds encompassed by the present invention are represented by the general formula (I):

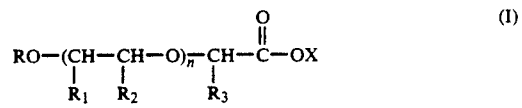

wherein R is a hydrocarbyl containing 1 to 44 carbons, $R_1$, $R_2$ and $R_3$ are independently hydrogen or an alkyl moiety containing 1 to 21 carbons, n is in the range of from 1 to 20, and X is a cation.

The substituent groups for the above formula (I) will now be described in greater detail in order to disclose and describe a representative number of examples of additive compounds of the invention and disclose preferred and particularly preferred embodiments.

In formula (I) and elsewhere in the disclosure hydrocarbyl means "hydrocarbon-based." As used herein, the term "hydrocarbon-based," "hydrocarbon-based substituent" and the like denotes a substituent having a carbon atom directly attached to the remainder of the molecule and having predominantly hydrocarbyl character within the context of this invention.

Examples of hydrocarbyl substituents which might be useful in connection with the present invention include the following:

(1) hydrocarbon substituents, that is, aliphatic (e.g., alkyl or alkenyl), alicyclic (e.g., cycloalkyl, cycloalkenyl) substituents, aromatic, aliphatic and alicyclic-substituted aromatic nuclei and the like as well as cyclic substituents wherein the ring is completed through another portion of the molecule (that is, for example, any two indicated substituents may together form an alicyclic radical);

(2) substituted hydrocarbon substituents, that is, those substituents containing nonhydrocarbon radicals which, in the context of this invention, do not alter the predominantly hydrocarbon substituent; those skilled in the art will be aware of such radicals (e.g., halo (especially chloro and fluoro), alkoxy, mercapto, alkylmercapto, nitro, nitroso, sulfoxy, etc.);

(3) hetero substituents, that is, substituents which will, while having predominantly hydrocarbyl character within the context of this invention, contain other than carbon present in a ring or chain otherwise composed of carbon atoms. Suitable heteroatoms will be apparent to those of ordinary skill in the art and include, for example, sulfur, oxygen, nitrogen and such substituents as, e.g., pyridyl, furanyl, thiophenyl, imidazolyl, etc., are exemplary of these hetero substituents.

In general, no more than about three radicals or heteroatoms and preferably no more than one, will be present for each ten carbon atoms in the hydrocarbon-based substituents. Typically, there will be no such radicals or heteroatoms in the hydrocarbon-based substituent and it will, therefore, by purely hydrocarbon.

Referring to formula I above, some specific examples of preferred R groups include the following:
1) Alkylated aromatics like dodecylphenyl
2) $C_{12-22}$ linear alkyl
3) $C_{10-18}$ branched alkyl
4) $C_{12}$-$C_{40}$ 2-alkyl,alkyl The above groups include the following R groups which are particularly preferred:
1) iso-stearyl;
2) $C_{24-28}$ alkylphenyl
3) $C_{16-18}$ alkyl
4) $C_{16-28}$ 2-alkyl, alkyl An additive included in a function fluid or lubricant oil will likely include a statistical mixture of compounds wherein the substituents of the different compounds vary in small increments over a range. For example, a statistical mixture of compounds might be present wherein the R group is an alkyl moiety containing 16 to 18 carbon atoms such that the average number of carbons is about 17.

$R_1$, $R_2$ and $R_3$ are independently hydrogen or an alkyl moiety containing 1 to 21 carbons. The compound represented by formula (I) must be oil soluble or oil dispersible and this property is effected by the length of R, $R_1$, $R_2$, and $R_3$. Accordingly, as the number of carbons in R is decreased below a certain point, the number of carbons in $R_1$, $R_2$ and/or $R_3$ must be increased to provide for oil solubility of the compound (I).

The present inventors point out that the compound (I) must be oil soluble in the final composition. However, compound (I) may not be soluble in oil by itself and have its solubility effected by other additives present in the final composition. Further, the compound (I) may be merely dispersible in a given concentrate but become dissolved as the proportional amount of oil is increased.

Compounds of formula (I) are preferably dispersable in oil either by themselves or in the presence of any other additive components and are more preferably readily soluble in oil either by themselves or in the presence of any other additive component normally present in oil.

Some typical examples of $R_1$, $R_2$ and $R_3$ include H, $CH_3$, $C_2H_5$ and other straight and branched chain alkyl groups containing up to about 21 carbons. Preferably, one of $R_1$, $R_2$ or $R_3$ is hydrogen. At least one of $R_1$ or $R_2$ should be hydrogen. When $R_1$, $R_2$ and $R_3$ are not hydrogen a $CH_3$ moiety is preferred. In one preferred embodiment $R_1$ and $R_3$ are hydrogen and $R_2$ is methyl, it is particularly preferred if $R_1$, $R_2$, and $R_3$ are all hydrogen.

The variable n can range from 1 to about 20. Although n is an integer for any particular molecule, it should be pointed out that any given sample of compound (I) is likely to include a number of molecules of (I) wherein n varies from one molecule to the next in increments over a range resulting in a statistical average for all the molecules. Accordingly, a sample may result wherein n is not a whole number, e.g., n is 4.5. Although n might be 1 to 20, it is preferably 4 to 6 and more preferably 5 for obtaining improvement in water tolerance and antiwear properties in a lubricant. Stating that n is preferably 5 means that a preferred composition includes molecular which have a statistical average for their n values of about 5.

The variable X may be any cation and includes cations of H, Ca, Mg, Na, Zn, Ba, Li, K or $NH_4$ diethyl amine and and triethyl amine. Preferred examples of X include cations of Ba, Na, Ca, Mg, and Zn. The inventors have found that X is most preferably a Ca or Mg cation.

Some specific examples of compounds of formula (I) include: iso-stearylpentaethyleneglycol-acetic acid; iso-stearyl—O—$(CH_2CH_2O)_5CH_2CO_2Na$; lauryl—O—$(CH_2CH_2O)$ 2.5—$CH_2CO_2H$; lauryl—O—$(CH_2CH_2O)_{3.3}CH_2CO_2H$; oleyl—O—$(CH_2CH_2O)_4$—$CH_2CO_2H$; lauryl—O—$(CH_2CH_2O)_{4.5}CH_2CO_2H$; lauryl—O—$(CH_2CH_2O)$—$_{10}CH_2CO_2H$; lauryl—O—$(CH_2CH_2O)_{16}CH_2CO_2H$; octylphenyl—O—$(CH_2CH_2O)$ $_8CH_2CO_2H$; octylphenyl—O—$(CH_2CH_2O)_{19}CH_2CO_2H$; 2-octyldecanyl—O—$(CH_2CH_2O)_6CH_2CO_2H$. Various salts, including overbased salts of the above acids are also examples of compounds of formula (I).

The terms "overbased salt," "overbased salt complex" and "basic salt" are used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 30° C. and filtering the resulting mass. The use of a "promoter" in the neutralization step to aid the incorporation of a large excess of metal likewise is known. Examples of compounds useful as the promoter include phenolic substances such as phenol, naphthol, alkylphenols, thiophenol, sulfurized alkylphenols, and condensation products of formaldehyde with phenolic substances; alcohols such as methanol, 2-propanol, octyl alcohol, Cellosolve, Carbitol, ethylene glycol, stearyl alcohol and cyclohexyl alcohol; and amines such as aniline, phenylenediamine, phenothiazine, phenyl-betanaphthylamine and dodecylamine. A particularly effective methods for preparing the basic salts comprises mixing an acid with an excess of a basic alkaline earth metal neutralizing agent and at least one alcohol promoter, (preferably methanol mixed with other alcohols like hexanol and amyl alcohols) and carbonating the mixture at an elevated temperature such as 30° to 200° C. Overbased complexes are disclosed in U.S. Pat. No. 3,714,042 which is incorporated herein by reference to disclose such complexes. The salt is preferably present in the composition in an amount that the composition has a base number of about 50 to about 400 TBN, more preferably about 100 to about 300 TBN.

Compositions of the present invention may be sold in concentrates in a diluent oil, in combination with any other known additive which includes, but is not limited to, dispersants, detergents, antioxidants, antiwear agents, extreme pressure agents, emulsifiers, demulsifiers, friction modifiers, anti-rust agents, corrosion inhibitors, viscosity improvers, dyes, and solvents to improve handleability which may include alkyl and/or aryl hydrocarbons. These additives may be present in various amounts depending on the needs of the final product.

The concentrate might containing 50% to 90% by weight of the compound of formula (I). The compound of formula (I) may be present in a final product, in an amount in the range of from about 0.01% to about 20% by weight based on the weight of the composition. As pointed out above the additive compound of formula (I) is not generally present as a single molecule but rather as a statistical mixture of molecules varying slightly over a range. Such statistical mixtures are easier to produce than a pure form of any given single molecule and is believed to provide for improved performance.

The following examples are provided so as to provide those of ordinary skill in the art with a complete disclosure and description how to make compounds and compositions of the invention. These examples are not intended to limit the scope of what the inventors regard as their invention. Efforts have been made to insure accuracy with respect to numbers used (e.g. amounts, temperature, etc.) but some experimental errors and deviation should be accounted for. Unless indicated otherwise, parts are parts by weight, temperature is in degrees C, and pressure is at or near atmospheric.

EXAMPLE A

Charge a flask with 210 grams of isostearyl pentaethylene glycol acetic acid, 20 grams of ZnO and 100 grams of toluene. Heat the mixture to 110° C. Continue heating in order to take off about 15 ml of azeotroped water and allow to cool. Remove the solvent by means of a Dean-Stark trap and heat the mixture to 160° C. for 4 hours. Cool the mixture to 120° C. and filter the reaction mixture over DD1600. Refilter the filtrate and wash the pad with toluene. Concentrate the filtrate under vacuum and collect the residue in the form of a zinc salt of the starting acid.

EXAMPLE B

Charge a flask with a mixture of compounds encompassed by general structural formula (I) wherein X is Na, n is 5, $R_1$, $R_2$ and $R_3$ are hydrogen and R contains 16–18 carbon atoms and may be branched or straight. Combine the mixture of compounds of structural formula (I) in an amount of 793 grams with 300 ml of toluene and heat the mixture in order to azeotrope off about 50 ml of water. Allow the mixture to cool and then reheat to about 80° C. and add 89.4 grams of $CaCl_2$ dissolved in 80 grams of water. Heat the mixture at 100° C. in order to azeotrope off about 80 ml of water and add toluene to the reacting mixture. Filtering can be carried out as indicated in Example A above in order to collect a calcium salt filtrate.

EXAMPLE C

Charge a flask with a compound encompassed by general structural formula (I) wherein X, $R_1$, $R_2$ and $R_3$ are hydrogen, n is 5 and R is alkyl and varies over a range of 6–18 carbons. The compound of structural formula (I) should be added in an amount 250 grams to a flask along with 86 grams of $Ca(OH)_2$ and 25 grams of a polyisobutylene substituted maleic anhydride, 120 grams of methanol, 248 grams of diluent oil and a 1000 grams of toluene. The mixture is to be heated in a flask to 45° C. and carbon dioxide gas bubbled through the mixture. Add 86 grams of $Ca(OH)2$ and discontinue the bubbling of the carbon dioxide. Heat the mixture to 150° C. in order to remove water and remove water and methanol via a Dean Stark trap. Centrifuge the mixture and decant off organic material. Add 26 grams of the polyisobutenyl substituted maleic anhydride and concentrate the mixture by heating to 110° C. at 30–40 mmHg.

EXAMPLE D

Charge a flask with a statistical mixture of compounds encompassed by general structural formula (I) wherein X, $R_1$, $R_2$ and R are hydrogen, n varies over a range to provide an average of about 5 and R is propyl. The mixture of compounds of structural formula (I) should be added in an amount 250 parts to a flask along with 50 parts of $Ca(OH)_2$ and 100 parts of methanol, 200 parts of diluent oil and 1000 parts of toluene. Heat the mixture in a flask to about 45° C. and bubble carbon dioxide gas through the mixture for about 30 minutes. Additional 50 part incremental amounts of $Ca(OH)_2$ are added and carbon dioxide bubbling is carried out with the addition of each incremental amount of $Ca(OH)_2$. When the desired amount of overbasing has been obtained by the addition of incremental amounts of $Ca(OH)_2$, heat the mixture to 150° C. in order to remove water and methanol via a Dean Stark trap. Centrifuse the mixture and decant off organic material.

EXAMPLE E

Charge a flask with a compound encompassed by general structural formula (I) wherein X, $R_1$, $R_2$ and $R_3$ are hydrogen, n is 5 and R is aromatic. The compound of structural formula (I) should be added in an amount 100 parts to a flask along with 25 parts of $Ca(OH)_2$ and 50 parts of an alcohol promoter which is 50% methanol, 25% hexanol and 25% amyl alcohols, 100 parts of diluent oil and 400 parts of toluene. Heat the mixture in a flask to 45° C. and bubble carbon dioxide gas through the mixture for 30 minutes. Add additional incremental amounts of $Ca(OH)_2$ (25 parts each) with heat and $CO_2$ bubbling with each addition until the desired base number is obtained. A high degree of overbasing can be obtained by this method. Heat to 150° C. with $N_2$ bubbling in order to remove water and alcohols. Filter to obtain product.

EXAMPLE F

Charge a flask with a mixture of compounds encompassed by general structural formula (I) wherein X is Na, $R_1$, $R_2$ and $R_3$ are hydrogen, n varies over a range of from 4 to 6 and R is an alkyl substituted aromatic. The compounds of structural formula (I) should be added in an amount 100 parts to a flask along 50 parts of calcium chloride. Then add 25 parts of Ca(OH)$_2$ and 50 parts of an alcohol promoter which is 50% methanol, 25% hexanol and 25% amyl alcohols, 100 parts of diluent oil and 400 parts of toluene. Heat the mixture in a flask to 45° C. and bubble carbon dioxide gas through the mixture for 30 minutes. Add additional incremental amounts of Ca(OH)$_2$ (25 parts each) with heat and CO$_2$ bubbling with each addition until the desired base number is obtained. A high degree of overbasing can be obtained by this method. Heat to 150° C. with N$_2$ bubbling in order to remove water and alcohols. Filter to obtain product.

EXAMPLE G

Charge a flask with a compound encompassed by general structural formula (I) wherein X and R$_1$ are hydrogen and R$_2$ and R$_3$ are methyl, n provides a statistical average of 5 and R is isostearyl. The compound of structural formula (I) should be added in an amount 100 parts to a flask along with 25 parts of Ca(OH)$_2$ and 100 parts of an alcohol promoter which is 40% methanol, 20% hexanol and 40% amyl alcohols, 100 parts of diluent oil and 400 parts of toluene. Heat the mixture in a flask to 45° C. and bubble carbon dioxide gas through the mixture for 30 minutes. Add additional incremental amounts of Ca(OH)$_2$ (25 parts each) with heat and CO$_2$ bubbling with each addition until the desired base number is obtained. A high degree of overbasing can be obtained by this method. Heat to 150° C. with N$_2$ bubbling in order to remove water and alcohols. Filter to obtain product.

EXAMPLE 1

A concentrate containing the multi-functional additive component of the present invention can be prepared by adding the salt prepared in accordance with Example C above to 100 grams of a diluent oil. The diluent oil can be added to functional fluids in order to improve characteristics of the fluid. Specifically, the addition of 0.5 to 2.5% by weight of the salt prepared in Example C can be added to a functional fluid in order to improve the water tolerance of the fluid without adversely affecting anti-wear and extreme pressure characteristics.

EXAMPLES 2-6

In order to prepare examples 2, 3, 4, 5 and 6, add 1% to 2% by weight of the salts and/or mixed salts prepared in accordance with Examples A, B, C, D and E respectively to a suitable diluent oil of lubricating viscosity.

EXAMPLE 7

Prepare a salt of the acid encompassed by general structural formula (I) using the procedure of Example B above while including some components of structural formula (I) wherein R is an aromatic moiety and n ranges from 4-6. Add the salt obtained to diluent oil in sufficient amounts so that the salt becomes dissolved in the diluent oil to the extent that the oil is not cloudy. This concentrate can be added to a functional fluid such as a tractor fluid in order to improve water tolerance characteristics of the tractor fluid. The concentrate should be added so that the salt present in the concentrate is ultimately present within the functional fluid in an amount of about 0.5% to about 2.5% based on the weight of the fluid.

EXAMPLES 8-14

Prepare examples 8, 9, 10, 11, 12, 13 and 14 respectively, by adding 0.1 parts to 20 parts of the salt and/or mixed salt of examples A, B, C, D, E, F, G to a suitable oil of lubricating viscosity. The amount of salt of examples A-G to be added varies depending on the end need requirements of the lubricant.

It should be noted that each of the salts described above in Examples A-C can be converted to concentrates by adding these salts to diluent oils. Further, these concentrates can be formed into additive package concentrates by combining the salt and diluent oil with any combination of know additives such as dispersants, detergents, antioxidants, antiwear-agents, extreme pressure agents, emulsifiers, demulsifiers, friction modifiers, anti-rust agents, corrosion inhibitors, viscosity improvers, dyes, solvents and other known additive components. These concentrates and/or concentrate packages can be added to functional fluids such as hydraulic fluids and/or tractor fluids in order to improve characteristics of the fluids such as to improve the water tolerance properties of the functional fluid.

The present invention has been disclosed and described herein in what is believed to be its preferred embodiments. However, modifications will occur to those skilled in the art upon reading this disclosure and such modifications are intended to be encompassed by the present invention.

What is claimed is:

1. An oil composition comprising:
   an oil of lubricating viscosity in an amount of 50% or more by weight based on the total weight of the composition, and
   a minor amount, sufficient to improve performance characteristics of the composition, of a calcium, magnesium, zinc, barium, ammonium, diethylamine, or triethylamine salt of a compound having structural formula (I)

RO—(HC(R$_1$)HC(R$_2$)O)$_n$C(R$_3$)H—COOH    (I)

wherein R is a hydrocarbyl group containing 1-44 carbon atoms, R$_1$ and R$_2$, are hydrogen, R$_3$ is hydrogen or an alkyl moiety containing 1-21 carbon atoms, and n is 1-20.

2. The composition of claim 1 wherein R contains 12-24 carbon atoms and R$_3$ is hydrogen.

3. The composition of claim 1 wherein n is 1-6.

4. The composition of claim 1 wherein n is 4-6 and the salt is a calcium, magnesium, or zinc slat.

5. The composition of claim 1 wherein R$_3$ is hydrogen and the salt is a calcium salt.

6. The composition of claim 1 wherein the salt is a mixture of materials having an average value of n of about 5, the salt is a calcium salt, and the salt is present in an amount of about 0.1 to about 20% by weight based on the total composition, and the composition has a base number of about 50-400 TBN.

7. The composition of claim 1 further comprising: a viscosity improver in an amount of about 0.3 to about 2 weight percent; an antiwear agent in an amount of about 0.5 to about 3 weight percent; and a nitrogen-containing dispersant in an amount of about 1 to about 15 weight percent.

8. The composition of claim 1 further comprising: a detergent in the amount of about 0.2 to about 7 weight percent, said detergent comprising a magnesium salicylate and an overbased calcium sulfonate; and an antifoaming agent in the amount of about 50 to about 200 parts per million.

9. An oil based composition comprising:
a base oil lubricating viscosity having therein about 0.5% to about 5% by weight of a calcium, magnesium, zinc, ammonium, diethylamine, or triethylamine salt of a compound of formula (II)

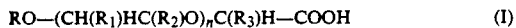
$$RO-(CH_2CH_2O)_n-CH_2COOH \qquad (II)$$

wherein n is about 5 and R is an alkyl group containing 6 to 24 carbon atoms.

10. The composition of claim 1 wherein the compound (II) is present at about 0.5% to bout 3% by weight and the salt is a calcium salt.

11. The composition of claim 1 wherein the compound (II) is present in an amount of about 0.5% to about 2% by weight, the salt is a calcium salt, and the composition has a base number of about 50 to about 400 TBN.

12. An oil additive concentrate comprising:
about 10% to about 50% by weight of an oil of lubricating viscosity; and
about 50 to 90% by weight of a calcium, magnesium, zinc, barium, ammonium, diethylamine, or triethylamine salt of a compound having the structural formula (I)

$$RO-(CH(R_1)HC(R_2)O)_nC(R_3)H-COOH \qquad (I)$$

wherein R is a hydrocarbyl containing 1 to 44 carbon atoms, $R_1$ and $R_2$ are hydrogen and $R_3$ is hydrogen or methyl, and n is 1–20.

13. The oil additive concentrate of claim 12 where R is a hydrocarbon group containing 6–22 carbon atoms and wherein the salt is a mixture of materials having an average value of n of about 5, and the composition has a base number of about 50–400 TBN.

14. The oil additive concentrate of claim 12 wherein the salt is a calcium salt.

15. The oil additive concentrate of claim 12 wherein the salt of the compound of formula (I) is a slat of isostearylpentaethyleneglycolacetic acid and is present at about 60% to about 90% based on the total weight of the concentrate.

16. The oil additive concentrate of claim 12 further comprising: a viscosity improver in the form of a hydrogenated butadiene/styrene copolymer; an anti-wear agent in the form of a zinc dithiophosphate compound; and a dipsersant.

17. The oil additive concentrate of claim 16 wherein the dispersant is a hydrocarbyl substituted succinimide.

18. The oil additive concentrate of claim 12 further comprising: a detergent in the form of an overbased magnesium salicylate and an overbased calcium sulfonate; and an antifoaming agent.

19. The oil additive concentrate of claim 12 further comprising a detergent selected from the group consisting of an ashless phenate and an overbased phenate.

20. The oil additive concentrate of claim 12 wherein the composition has a base number of about 100–300 TBN.

* * * * *